United States Patent [19]

Gourgouliatos et al.

[11] Patent Number: 5,709,459
[45] Date of Patent: Jan. 20, 1998

[54] SURGICAL LUMINAIRE

[75] Inventors: Zafirios Gourgouliatos, Los Angeles; Mark D. Hopler, Valencia; Kenneth Li, Arcadia, all of Calif.

[73] Assignee: Cogent Light Technologies, Inc., Santa Clarita, Calif.

[21] Appl. No.: 347,709

[22] Filed: Dec. 1, 1994

Related U.S. Application Data

[63] Continuation-in-part of Ser. No. 134,262, Oct. 8, 1993, Pat. No. 5,430,620.

[51] Int. Cl.⁶ .................................................. F21L 15/14
[52] U.S. Cl. .......................... 362/105; 362/32; 362/277; 362/804
[58] Field of Search .......................... 362/19, 32, 105, 362/106, 268, 277, 319, 804; 600/160

[56] References Cited

U.S. PATENT DOCUMENTS 1,042,716 10/1912 Myers ............................ 362/268
3,285,242 11/1966 Wallace .......................... 362/105
3,745,993  7/1973 Feinbloom ...................... 362/105
4,516,190  5/1985 Kloots ............................ 362/106
4,759,615  7/1988 Bainbridge ....................... 362/32
4,807,092  2/1989 Hasegawa ........................ 362/32
4,970,631 11/1990 Marshall ......................... 362/105
5,430,620  7/1995 Li et al. .......................... 362/105

*Primary Examiner*—Y My Quach
*Attorney, Agent, or Firm*—Rothwell, Figg, Ernst & Kurz, P.C.

[57] ABSTRACT

A luminaire for use during a medical procedure utilizes a single optic fiber for providing a beam of light having an initial beam width and an initial beam energy. The width of the beam is adjustable without substantially decreasing the beam energy, and the beam of adjusted width can be directed onto a surgical field. A headband for mounting a luminaire is formed of a perspiration-absorbent cloth strip, has hook-and-clasp engagement, and includes a luminaire mount.

18 Claims, 5 Drawing Sheets

SURGICAL LUMINAIRE

RELATED APPLICATION

This application is a continuation-in-part of U.S. Ser. No. 08/134,262, filed Oct. 8, 1993, now U.S. Pat. No. 5,430,620, issued Jul. 4, 1995.

BACKGROUND OF THE INVENTION

1. Field of the Invention

The invention generally relates to medical illumination systems and in particular to a surgical head light or luminaire for use by a surgeon to illuminate a portion of a surgical field such as a portion of a patient being operated upon.

2. Description of Related Art

A variety of surgical luminaires have been developed for use by surgeons or other medical personnel during medical procedures. A surgical luminaire provides a system for illuminating a small portion of the surgical field in which the surgeon is operating. For example, a luminaire may illuminate a 10-150 millimeter diameter portion of tissue that a surgeon is inspecting or operating upon.

A typical luminaire mounts over the forehead of the surgeon by means of a strap or other mechanical harness fitted around the surgeon's head. The luminaire receives light from a remote source of illumination through a fiber optic bundle. Light provided by the fiber optic bundle is directed generally downwardly along an optical axis through an interior portion of the luminaire to an angled mirror. The light is reflected off of the angled mirror into the surgical field. Examples of conventional luminaires are disclosed in U.S. Pat. No. 3,285,242 to Wallace and U.S. Pat. No. 4,516,190 to Kloots. A luminaire is typically used in conjunction with a surgical loupe which allows the surgeon to view the illuminated surgical field with magnification.

It is desirable to allow the size of the illuminated spot to be varied during a surgical procedure, perhaps to allow the surgeon to isolate more effectively a particular portion of the surgical field. One mechanism for allowing the spot size to be adjusted employs an iris mounted within the luminaire at an internal focal plane. A mechanical arrangement is provided for varying the interior diameter of the iris to vary the spot size. The luminaire of the Kloots patent employs an iris. The use of an iris, however, has certain disadvantages. The iris reduces the spot size by blocking a portion of the light. For the smallest spot sizes, the amount of illumination remaining may be inadequate. Moreover, because the iris is positioned at an internal focal plane, the iris itself is imaged into the surgical field thereby creating a non-uniformly illuminated spot. In other words, the actual shape of the iris, which is typically polygonal, is imaged and focused onto the surgical field. The polygonal outline of the image of the iris can distract the surgeon. Furthermore, any dust or other particles on the iris or in the vicinity thereof are likewise imaged onto the surgical field providing a further distraction to the surgeon. The luminaire of the Wallace patent employs a mechanism to adjust the spot size by varying the distance of a field lens from a diffusing lens. The diffusing lens is required to eliminate imaging of the fibers within the multiple fiber bundle light delivery system. Fiber bundles are less efficient in transmitting light and require larger optics to transmit the light to the surgical field. The luminaire is less efficient, as a result, in delivering light and the optical requirements are different because a bundle is effectively an extended source.

By contrast, the present invention includes a single fiber optic light delivery system that behaves optically as a point source, does not require a diffuser to eliminate optical imaging of multiple fibers in a bundle, and can be optically attached to a lensing system with high efficiency. The lensing system of the present invention creates an improved method of varying the spot size. The lenses are configured and positioned to allow the size of the spot to be varied by varying the relative distance between the lenses. In this manner, spot size variation is achieved without imaging a mechanical iris and the disadvantages associated therewith are avoided.

An alternative system for varying the spot size is described in co-pending U.S. patent application Ser. No. 08/134,262, U.S. Pat. No. 5,430,620, entitled "Compact Surgical Illumination System Capable Of Dynamically Adjusting The Resulting Field Of Illumination", to Li et al., filed Oct. 8, 1993. The system described therein provides a single lens within the luminaire placed along the optical axis of a single fiber optic. A mechanism is provided for displacing the lens with respect to the fiber optic to change the focal length of the overall optical system and thereby vary the spot size. As such, the system eliminates some of the problems associated with the use of a mechanical iris. However, other significant disadvantages remain, creating less than optimal optical efficiencies.

Some of the disadvantages of systems employing a single lens in combination with a single fiber optic are as follows. A first disadvantage is that it is difficult to match the numerical aperture (NA) of the fiber to that of the lens. A single fiber optic having a high NA requires a lens also having a high NA to capture light output from the single fiber optic efficiently. The use of such a powerful lens, however, results in significant spherical and chromatic aberration. If a somewhat less powerful lens is employed, the amount of spherical or chromatic aberration may be decreased, but significant light loss can occur which both decreases the amount of light available for illuminating a spot and also heats the interior of the luminaire, perhaps to the point of damaging internal components. A second significant disadvantage is that the range of spot sizes which can be achieved with adequate illumination using a single lens system is limited. In particular, it is difficult to achieve an adequate light gathering capability for a wide range of spot sizes. The light gathering ability is defined by the NA of the system. The NA can be increased only by either reducing focal length or increasing aperture size. A reduction in focal length however results in a fairly dim spot illumination. An increase in the aperture size results in a high overall system size and weight. Hence, for practical systems incorporating a single lens and a single fiber optic, it is difficult to achieve a wide range of spot sizes while maintaining an adequate light gathering capability. A third disadvantage of employing a single fiber optic and a single lens is that it is difficult, from a design and engineering standpoint, to configure a surgical luminaire for mounting to the forehead of a surgeon which directs light from the single lens coaxial with the surgeon's vision into a surgical field. In particular, it is desirable that light transmitted into the surgical field be provided along the surgeon's plane of vision so that observation inside a small incision has adequate illumination. With the luminaire mounted to the head of a surgeon, coaxial illumination requires that a mirror be provided for reflecting light into the surgical field. It is difficult to provide a simple and lightweight system which incorporates the single fiber optic, the lens, the mirror and an adjusting mechanism to vary spot size while also providing a high degree of efficiency in light delivery.

The two lens system of the invention overcomes these various disadvantages. As will be described more fully below, the two lens system achieves a high NA while avoiding the light loss problems associated with a single lens system. Also, by providing a pair of lenses which can be displaced one from the other, the range of spot sizes can be conveniently varied using small and lightweight lenses. The use of small and lightweight lenses allows the overall luminaire to be likewise small and lightweight and further allows the aforementioned design and engineering problems to be substantially avoided.

As noted, typical luminaires direct a beam of light along an internal optical axis of the luminaire onto a mirror for reflection into a surgical field. The mirror is typically mounted such that an angle between a normal of the mirror and the optical axis of the luminaire is 45°. As such, the reflected beam of light appears within the surgical field at a position 90° from the internal optical axis of the luminaire. The surgical field is typically beneath and somewhat in front of the head of the surgeon. To allow the surgical field to be illuminated, the luminaire is typically mounted at an angle with respect to the face of the surgeon. In particular, a top portion of the luminaire is tilted outwardly by a significant amount, to pivot the reflecting mirror inwardly to allow a portion of the surgical field beneath the surgeon to be illuminated properly. This outward tilting of the top of the luminaire can be uncomfortable and obstructive for the surgeon. Moreover, with the top portion of the luminaire tilted outwardly by a substantial amount, the luminaire can be unintentionally bumped by other medical personnel. Such requires realignment of the luminaire causing a delay which may have serious consequences if occurring during a critical portion of a surgical procedure. The problem is even more severe with luminaires having a fiber optic bundle feeding into a top portion of the luminaire. With the luminaire tilted outwardly, the fiber optic bundle is likewise tilted outwardly resulting in an even greater risk of accidental mis-alignment. It would be desirable to provide a luminaire which need not be tilted away from the face of the surgeon yet which can illuminate a surgical field which is beneath and somewhat in front of the surgeon.

In accordance with another aspect of the invention, described more fully below, a luminaire is provided with a mirror mounted such that an angle between a normal to the mirror and the optical axis of the luminaire is 60°. As such, the light beam is reflected more downwardly than in conventional systems. This configuration allows the luminaire itself to be mounted substantially vertically adjacent to a surgeon's forehead while illuminating a spot within a surgical field which is below and somewhat in front of the surgeon. In other words, the top position of the luminaire need not be pivoted outwardly as in conventional systems.

Another disadvantage with conventional luminaires is that the optical characteristics of the source of illumination cannot be selectively controlled or varied. A typical luminaire system employs an external illumination source providing light having only a single predetermined optical spectrum or characteristic "color temperature". The color temperature characteristic may vary from system to system. As such, a surgeon trained on one system may be at a disadvantage when employing a different luminaire system. For example, the surgeon may be accustomed to distinguishing between diseased tissue and healthy tissue based upon slight color variations. Such variations may appear differently when using a luminaire system having a different source of illumination. As an example, many surgeons have been trained using illuminators which produce a somewhat yellowish color. The somewhat yellowish color occurs, in part, because a fiber optic bundle is employed which tends to absorb short wavelength light, such as a bluish light, thereby emitting a somewhat yellowish light beam. Cogent Light Technologies, assignee of rights to the present application, provides an improved illumination system which emits, from a single fiber, a high intensity beam of white light of similar color temperature as the sun. Light transmitted through this fiber optic does not vary in color. Although the color temperature of the light is advantageous for many applications, some surgeons may find it desirable to vary the color of the beam to match the yellowish light beams that they are accustomed to using. Alternatively, a surgeon may simply wish to use a different colored beam of light to help emphasize aspects of the surgical field. In either case, it would be desirable to allow the optical characteristics of the beam of illumination provided by the luminaire to be varied. In accordance with yet another aspect of the invention, the foregoing is achieved by providing a filter within an output aperture of the luminaire.

In circumstances where the surgical field is covered with a thin layer of clear liquid, perhaps water, it is often difficult for the surgeon to see through the layer of liquid and into the tissues of interest. This is particularly a problem if light glares off of the liquid. It would be desirable to provide a mechanism for eliminating glare and for otherwise allowing the surgeon to see more clearly into the tissues of interest. Dr. R. Rox Anderson of Wellman Labs of Photo Medicine, Massachusetts General Hospital, Harvard Medical School has demonstrated that the polarization of light affects the ability to see into tissues of interest. In accordance with one aspect of the invention, a polarizer is provided on a luminaire and polarizers are likewise provided on surgical loupes used by the surgeon. The polarizer on the head light is rotatable to adjust selectively the degree of filtering of polarized light to allow the surgeon to more clearly see into tissues of interest.

SUMMARY OF THE INVENTION

The invention is a head light system that provides the following advantages, among others. The luminaire is lightweight, small, and relatively unobstructive. It is powered by a single fiber optic light delivery system equivalent to a point source. As a result, the luminaire is configured to provide for easy adjustment of the spot size while achieving high optical efficiency. The system also includes color filters allowing a surgeon or other person utilizing the system to vary the spectral characteristics of a light beam emitted by the system. The luminaire can also be configured with a polarizer filter and used in conjunction with surgical loupes also having polarizer filters to allow the surgeon to selectively filter polarized light to see more clearly into tissues of interest.

These and other advantages are achieved by the invention as follows. In accordance with one aspect of the invention, a head light is provided with a pair of lenses positioned along an optical axis of a light transmitting single optical fiber. Means are provided for allowing the spacing between the pair of lenses to be varied to adjust the size of the illuminated spot. The lensing system generates a more uniform spot compared with a mechanical iris as the size of the spot decreases. Compared with a single lens, a pair of lenses produces much higher overall optical efficiency and increased levels of illumination, for a given level of input from an optical fiber.

In accordance with another aspect of the invention, a luminaire is provided with a reflecting mirror having a normal oriented at an angle of about 60° from an optical axis of the luminaire. By orienting the reflecting mirror at 60°, rather than 45° as in prior art luminaires, the luminaire can illuminate a surgical field positioned substantially beneath the surgeon without requiring the luminaire to be tilted outwardly from the head of the surgeon. As such, the likelihood of the luminaire being misaligned, perhaps as a result of the luminaire being bumped against the luminaire of another surgeon, is significantly reduced.

In accordance with yet another aspect of the invention, a luminaire is provided with one or more optical filters mounted to an exit aperture of the luminaire between the reflecting mirror of the luminaire and the surgical field. With suitable choice of filters, the optical characteristics of the light provided by the luminaire can be varied either to enhance visible features within the surgical field or to compensate for differences in the source of light provided to the luminaire.

In accordance with another aspect of the invention, a luminaire is provided with a linear polarizer mounted to the exit aperture of the luminaire. A second linear polarizer is mounted to a surgical loupe used by the surgeon. One or both of the polarizers is rotatable. By providing a pair of linear polarizers, the amount of glare emanating from the surgical field can be substantially eliminated allowing the surgeon to see more clearly into the tissues of interest.

In accordance with one more aspect of the invention, a luminaire is provided with a fiber optic beam width reducer for mounting to the exit portion of an optic fiber and for reducing the width of an optical beam emitted therefrom. In a preferred embodiment, a secondary optic fiber of lesser diameter is coupled at its proximal end to a primary optic fiber. The optical axis of the secondary optic fiber has a distal end connected to the lensing system of the luminaire. As such, the width of the beam of light transmitted into the luminaire and reflected onto the surgical field is smaller. Hence, the minimum spot size which can be achieved using the luminaire is correspondingly smaller than that which could be achieved without the beam width reducer.

In an exemplary luminaire, described herein, each of the foregoing improvements are incorporated. In other embodiments, however, only one or two of the specific improvements are incorporated.

With these various improvements, the luminaire of the invention overcomes the disadvantages noted above. Accordingly, the general objectives set forth above are achieved. Other advantages, objects and features of the invention will be apparent from the figures which are attached hereto and from the descriptions which follow.

DETAILED DESCRIPTION OF THE INVENTION

Figure 1:
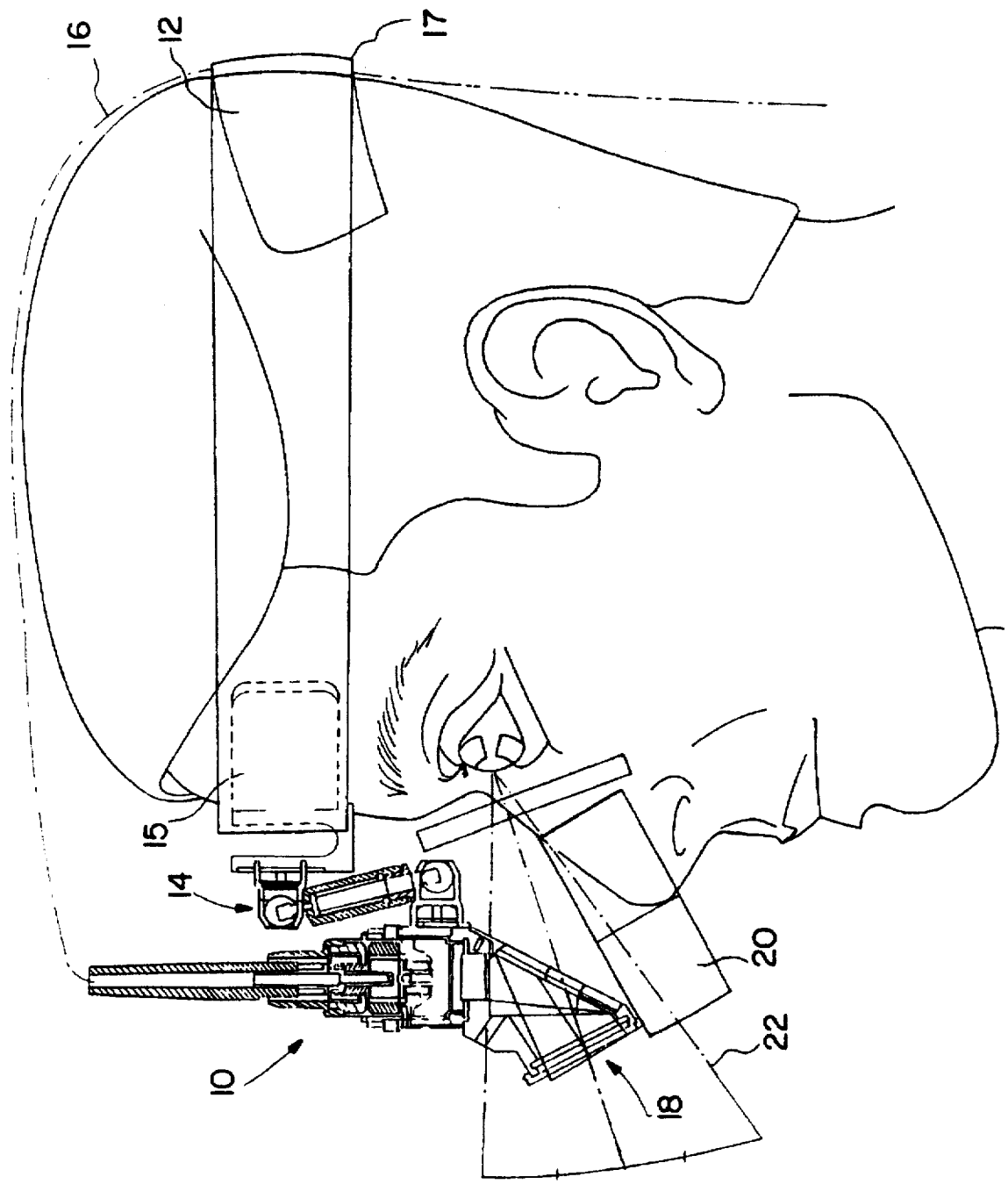
FIG. 1 is a side elevational view, partially in cross-section, showing a luminaire configured in accordance with the invention mounted to the head of a surgeon who is also utilizing a surgical loupe.

Referring to figures, embodiments of the invention will now be described. FIG. 1 illustrates a luminaire 10 mounted to the forehead of a surgeon by a mounting arrangement including a mounting strap 12 and a pivot attachment 14. Luminaire 10 receives a beam of light through a single optical fiber 16 and emits a beam of light for illuminating a spot within a surgical field through an exit aperture 18. As shown in FIG. 1, luminaire 10 may be used in combination with a surgical loupe 20. A line of sight through loupe 20 is identified by reference numeral 22. Among other improvements, luminaire 10 is configured to direct light along the same line as the loupes while remaining substantially vertical, as shown.

Figure 2:
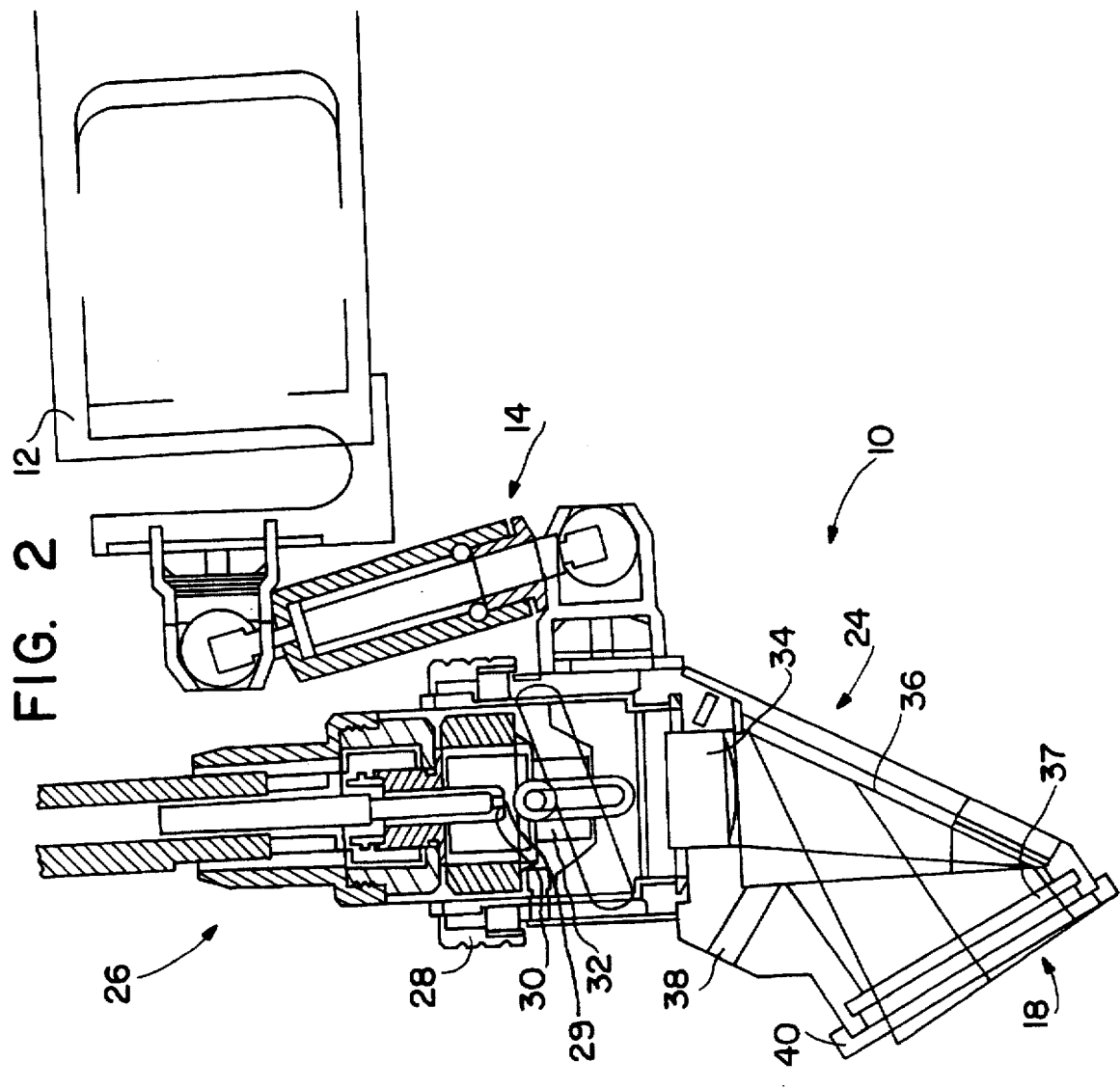
FIG. 2 is an enlarged cross-sectional view of the luminaire of FIG. 1.

FIG. 2 illustrates, in cross section, an enlarged portion of luminaire 10. Luminaire 10 includes a lower housing 24 and an upper housing 26. Lower housing 24 is mounted through pivot attachment 14 to head band 12. Upper housing 26 is mounted for displaceable movement with respect to lower housing 24. A knurled focus wheel 28 is mounted to a top exterior periphery of lower housing 24 where it engages a lower portion of upper housing 26. Rotation of focus wheel 28 causes upper housing 26 to be displaced along a vertical axis with respect to lower housing 24, thereby translating the lenses relative to one another. This is achieved without rotating either the fiber or the lenses.

A single fiber optic cable is received within an internal shaft of upper housing 26. An exit end 29 of the fiber optic cable is secured within a mounting element 30. Upper housing 26 also includes an optical lens system 32 mounted immediately below, and coaxial with, exit end 29 of the fiber optic cable. A second lens system 34 is mounted within lower housing 24. Lens system 34 is also coaxial with the optic axis defined by the optical fiber cable. The displacement of upper housing 26 with respect to lower housing 24 causes fiber optic exit end 29 and lens system 32 to be displaced with respect to lens system 34 thereby varying the degree of focus achieved by the overall optical system. As a result, the angular size of a cone of light emitted from the fiber optic cable and passing through lens systems 32 and 34 can be controlled by rotating focus wheel 28. The beam of light, after passing through lens system 34, reflects off of a mirror 36 through a window 37 mounted in exit aperture 18 and onto a surgical field (not shown). Mirror 36 is a first surface mirror which is 80–100% reflective over the usable band widths. It is positioned with its surface normal at a 60° angle to light exiting lower lens 34 for a total light bend of 120°. Front window 37 is glass and is positioned with its surface perpendicular to from light reflected from mirror 36. Preferably an anti-reflection coating is provided on window 37 to minimize reflection over the usable spectral band pass.

Lens systems 32 and 34 are positioned and configured to achieve a desired range of spot sizes within the surgical field. As an example, the lens systems can be arranged and configured to produce spot sizes varying from 20 millimeters to 100 millimeters in diameter at a distance of 16 inches from exit aperture 18. The largest spot size is achieved by positioning lens systems 32 and 34 close together. The smallest possible spot size is achieved by displacing upper lens 32 as far from lower lens system 34 as possible given the mechanical coupling arrangement.

Considering the relationship of lenses 32 and 34 in greater detail, a primary optical goal in the design of the exemplary luminaire of FIG. 1 was to maximize the throughput of light. This is achieved by providing for a large NA. The greatest optical efficiency is needed at the largest spot size to ensure an adequately bright, large spot. To achieve the greatest efficiency at the largest spot size, the lens system is configured to provide the largest spot size when the two lenses are close together, as such guarantees the least amount of light lost around the lenses. The fiber and lens 32 are moved away from lens 34 until the fiber exit aperture is almost imaged by the lens system as such provides the smallest spot that can be achieved without further aperturing of the optical system. It should be noted that during displacement of the fiber and lens 32, as the separation increases, more and more light is lost around lens 34. However, because of the decreasing spot size, the brightness of the illuminated spot actually increases. Hence the light loss around the lenses does not result in any dimming of the illuminated spot.

Lenses 32 and 34 are both achromatic doublet lenses, i.e., each consists of two lenses of differing glass types cemented together. The differing glass types are chosen to achieve color correction to reduce chromatic aberration. In an exemplary embodiment, lens 32 has a focal length of 12 millimeters and lens 34 has a focal length of 18 millimeters. The diameter of the curvature of lens 32 is 7 millimeters and the diameter of lens 34 is 9 millimeters. As noted above, the lenses are configured to provide a 100 millimeter spot at a distance of about 16 inches when the lenses are adjacent to one another. The lenses provide a smallest possible spot size of about 20 millimeters at the distance of 16 inches when lens 32 is displaced far enough from lens 34 to almost image the exit aperture of the optic fiber.

As noted, lens 32 and the fiber are coupled together and are displaced without rotation of either lens 32 or the fiber as such would cause an undesirable twisting of the fiber.

Hence, spot size adjustment is achieved without requiring the provision of an iris or an internal focal plane as required in certain prior art luminaires discussed above. Moreover, by providing a pair of lenses configured as shown, the overall optical efficiency of the luminaire may achieve 83% or more. In other words, 83% of the light emitted from the fiber optic cable reaches the surgical field. An optical efficiency of 83% is significantly greater than the efficiency that can be achieved with a single lens system which may be only about 40–50%.

Positioning of the spot within the surgical field is performed by manually readjusting the relative position of the luminaire with respect to the head band assembly 12. This may be facilitated by employing a joy stick (now shown in FIG. 2) which is mounted within shaft 38 of lower housing 24.

As noted, light provided by the optical fiber is reflected from mirror 36 through aperture 18. In the preferred embodiment, mirror 36 is mounted with a normal at an angle of 60° with respect to the optical axis of light emitted from the optic fiber. Hence, an angle between a beam incident to the mirror and a beam reflected from the mirror is 120°. In use, the luminaire is mounted such that the light reflected from mirror 36 is aligned along line of sight 22 (FIG. 1) along which the surgeon views the surgical field through the surgical loupe. It has been found that, by mounting the reflecting mirror at an angle of 60° with respect to the optical axis, the luminaire may be mounted substantially parallel with the face of the surgeon. In other words, an upper portion of the luminaire need not be tilted outwardly by a substantial amount as is required in the conventional luminaires described above. However, depending upon the particular orientation of the surgeon to the surgical field and depending upon the particular orientation of the surgical loupe, the position of the luminaire may need to be tilted by some modest amount with respect to the face of the surgeon. Moreover, although the embodiment described herein provides a reflecting mirror angled at 60° from the optical axis, other specific angles may be appropriate. In general, angles between 50° and 70° have been found to be effective with angle between 55 degrees and 65 (forming an included angle of 110 to 130 degrees between the incident light beam and the reflected beam) being preferred.

FIG. 2 also illustrates a filter 40 mounted to aperture 18. This may be achieved by a thread mounting mechanism as shown or by other mounting means as well. Filter 40 is provided for filtering the light illuminating the surgical field to alter the spectral characteristics or color temperature characteristics of the light. A wide range of filters having different spectral band pass characteristics may be provided for use with the luminaire. As noted above, conventional surgical luminaire systems receive light from a fiber optic bundle which varies the color of light output from a white light illumination system. Many surgeons have been trained using conventional systems which provide a colored illumination spot. The single fiber optic of the luminaire of the invention, however, does not vary the characteristics of light output from a white light source. As such, a spot produced by the luminaire of the invention is a white light spot. Surgeons trained using conventional systems may prefer to provide a filter to alter the color of the spot to conform with the somewhat yellowish illumination produced by conventional systems. Also, for a white light source (≈6000K) filters are particularly useful for adjusting the color of light to allow the surgeon to see more clearly tissues of interest within the surgical field. Use of filters may have other advantages as well.

Depending upon the medical procedure being performed and upon the preferences of the surgeon, a single filter may be mounted prior to the procedure and used throughout the procedure. Alternatively, filters may be manually changed during the medical procedure, perhaps by a nurse or other assistant to the surgeon.

As noted above, luminaire 10 is mounted to a mounting strap 12. More specifically, mounting strap 12 is a sweat band-style strap, preferably fabricated from terry cloth. A rear portion of the head band includes Velcro®-type patches for adjusting the tightness of the head band and for allowing the head band to be conveniently mounted and removed from the head. Pivot attachment 14 includes a rear plastic plate 15 contoured to generally match the curvature of a surgeon's forehead. A front portion of the head band is sewn to form a pocket into which the contoured plate is inserted.

Hence, a very lightweight and snug head band system is provided for mounting the luminaire to the head of a surgeon. This is in contrast with conventional systems which typically include a large heavy and cumbersome mechanical arrangement for mounting a conventionally-sized luminaire. The lightweight head band of the invention is sufficient, in part, because the luminaire itself is quite lightweight and therefore does not require any sturdy mounting arrangement.

The rear portion of the head band preferably includes a clasp 17 for receiving and securing the single fiber optic light guide. The clasp may likewise include a Velcro®-type mounting arrangement. The clasp allows the single fiber optic light guide to be secured at the rear of the head of the surgeon.

By forming the head band from terry cloth or similar fabrics, the head band also acts to absorb any perspiration from the surgeon.

Figure 3:
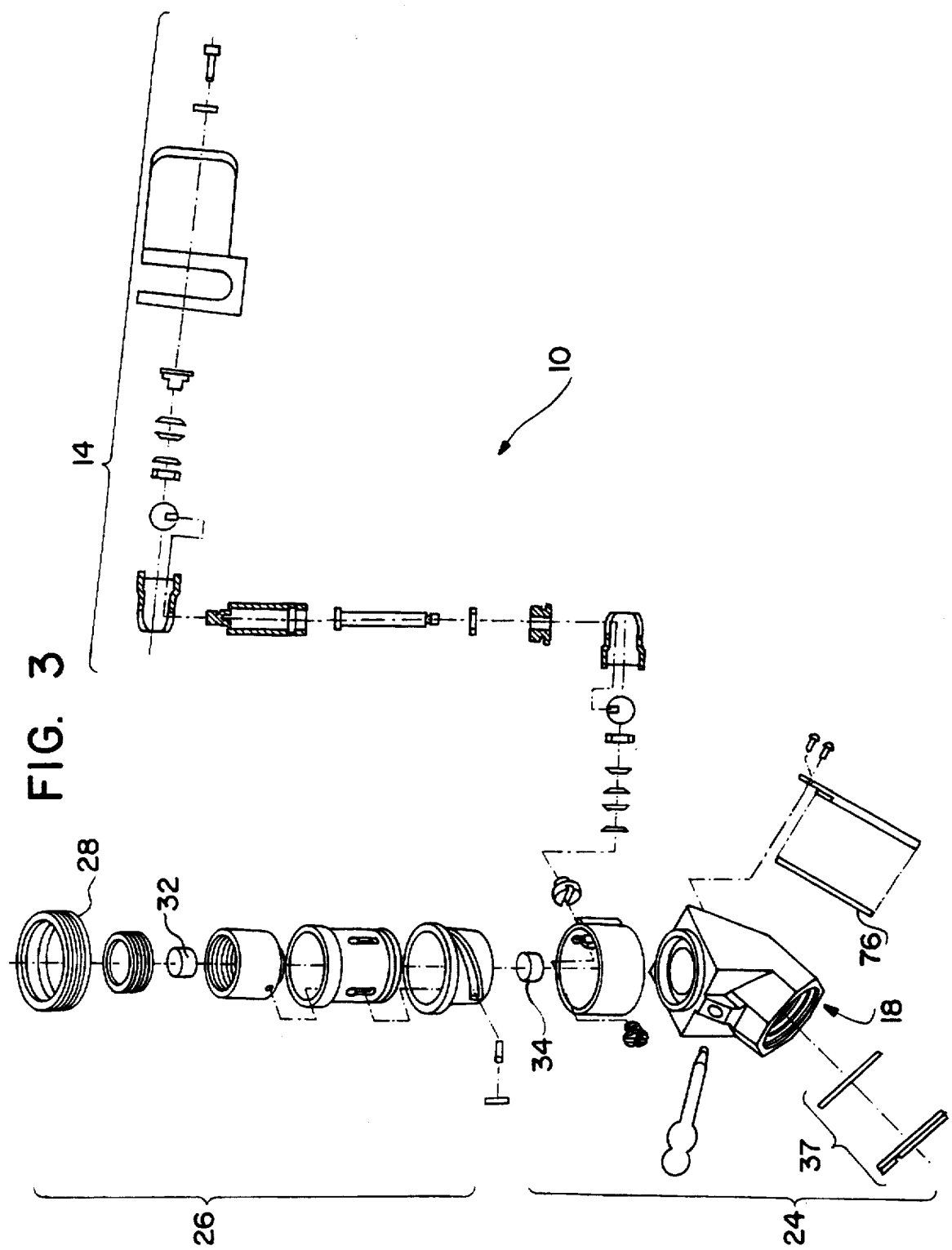
FIG. 3 is an exploded perspective view of the luminaire of FIG. 1.

FIG. 3 illustrates an exploded view of an exemplary head lamp illustrating each of the mechanical and optical components of a complete luminaire. FIG. 3 particularly illustrates how lenses systems 32 and 34 are mounted within lower and upper housings 24 and 26 and how lateral displacement of the lenses is achieved. The embodiment of FIG. 3 does not include the optional filter.

Figure 4A:
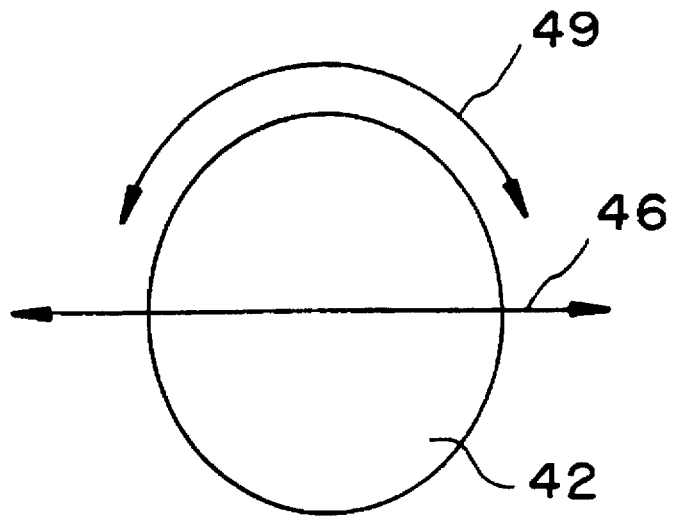
FIGS. 4(a) and 4(b) illustrate linear polarizer filters mounted to the luminaire and loupe of FIG. 1, respectively.
Figure 4B:
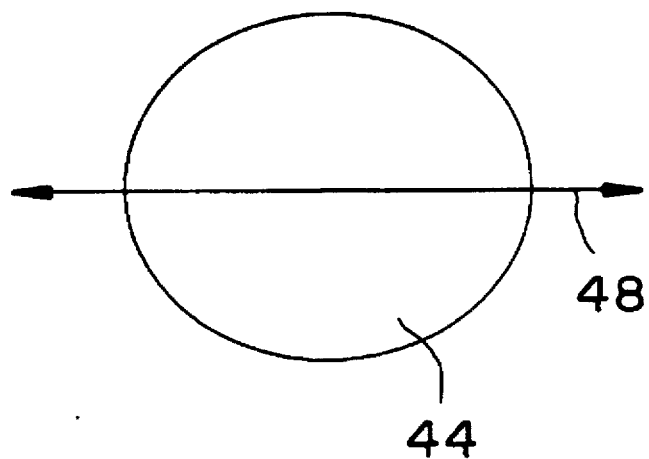

Referring to FIGS. 4(a) and 4(b), a pair of polarizer filters 42 and 44 are illustrated. Polarizer filter 42 is provided for mounting to aperture 18 (FIG. 2) of the luminaire. Polarizer 44 is provided for mounting to surgical loupe 20 (FIG. 1) or any other viewing device such as eyeglasses, safety glasses, splash guards, etc. FIGS. 4(a) and 4(b) also illustrate the angle of polarization 46 and 48 of filters 42 and 44, respectively. In the figures, the polarizers are oriented parallel with each other but one or both is preferably rotatable. Light provided by the luminaire through filter 42 and reflected from the surgical field is viewable through the surgical loupe. However, other sources of light, having generally different polarization characteristics, are substantially filtered by polarizer filter 44. In particular, light which is specularly reflected from the surgical field is substantially eliminated by filter 44. As such, glare is significantly reduced and the surgeon is able to more clearly view the surgical field. Although the pair of polarizer filters may be used in a variety of circumstances, their use is particularly desirable when the surgical field is covered by a thin layer of liquid which can result in significant glaring. Either the polarizer mounted to the luminaire or the polarizer mounted to the surgical loupe may be tilted or pivoted to adjust the polarization filtering of light. Depending upon the angle of illumination, optimal filtering may be achieved by orienting the polarizers such as they are not parallel to each other. In FIG. 4(a), an arrow 49 illustrates that the polarizer of the luminaire may be rotated.

Figure 5:
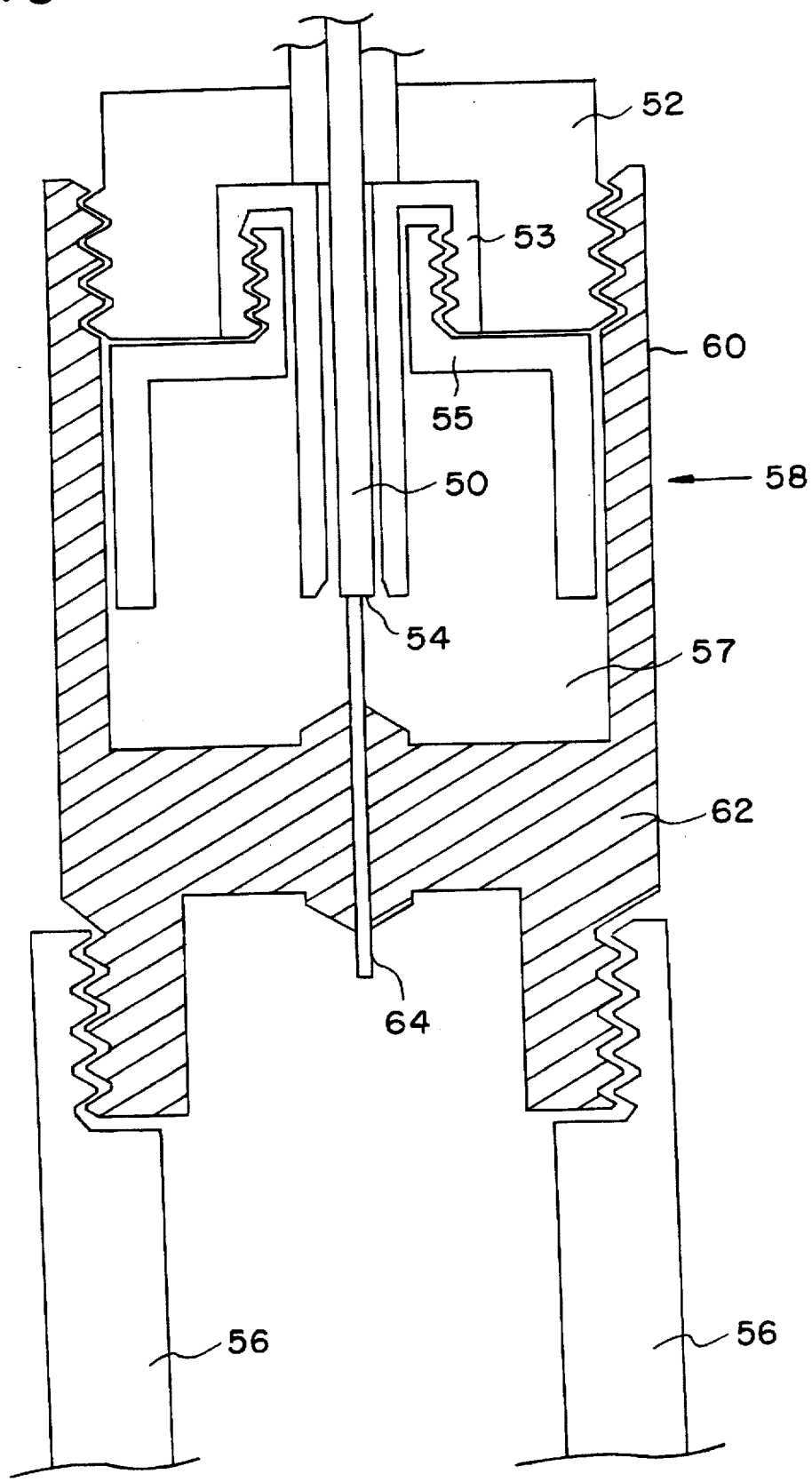
FIG. 5 is a close-up view, in cross-section, of the optic fiber mounting element of the luminaire of FIGS. 1-3 but provided with an optic fiber beam width reducing element.

As noted, the luminaire of FIGS. 1-3 allows the spot size to be adjusted by varying the spacing between lens systems 32 and 34 (FIG. 2). However, the minimum spot size is limited by the size of the exit aperture of the optical fiber. FIG. 5 illustrates a mounting system which allows the minimum spot size to be reduced. In particular, FIG. 5 illustrates the mounting arrangement for mounting a relatively thick optical fiber 50 within the luminaire. Optical fiber 50 includes a threaded mounting attachment 52, including subelements 53 and 55, affixed to the optical fiber. Without a reducer, threaded mounting member 52 is received within a threaded shaft 56 which forms a portion of upper housing 26 (FIG. 2) of the luminaire.

FIG. 5, however, illustrates a beam width reducer element inserted between optical fiber 50 and shaft 56. Reducer element 58 includes an upper portion 60 threaded for receiving threaded member 52 of the optical fiber. Reducer element 58 includes a lower portion 62 sized and threaded for mounting into shaft 56. Mounted within reducer element 58 is a relatively thin optical fiber 64 which receives a portion of the light emitted from an exit aperture 54 of optical fiber 50 and transmits the light into the interior of the luminaire along the optical axis. As such, the beam actually transmitted into the optical fiber for reflection onto the surgical field is considerably narrower than a beam provided by optical fiber 50. Hence, by inserting the beam width reducer 58 into the luminaire, the minimum spot size is reduced. It should be noted that an interior portion between reducer element 58 and threaded member 52 provides an empty volume or space 57 into which light that is not coupled into fiber 64 is scattered. Heat generated by light rays scattered therein is eventually dissipated by the components surrounding volume 57.

Although FIG. 5 illustrates one particular mounting arrangement for mounting optical fibers of different sizes, other mounting arrangements may be provided. If desired, the mounting arrangement may be configured for allowing the reducer element to be easily inserted or removed during a medical procedure to allow the minimum spot size to be easily adjusted. In still other embodiments, a set of reducer elements having internal optical fibers of differing thicknesses are provided such that a variety of minimum spot sizes, and corresponding maximum spot sizes, can be selected. In yet another embodiment, a pin hole aperture is provided with the pin hole aligned along the optical axis of light emitted from fiber 50. By selecting the position of the pin hole aperture between the end of the optic fiber and the lens system, the minimum spot size can also be reduced.

What has been described are preferred and exemplary embodiments of a luminaire having, among other features, an optical system for varying the spot size of a spot within a surgical field without the need for a mechanical iris and without a substantial loss in optical efficiency; a reflector mirror angled for reflecting an optical beam into a surgical field without requiting tilting of the luminaire with respect to the surgeon; optical filters including polarizing filters for varying the optical characteristics of light transmitted by the luminaire and viewed by the surgeon; and having a beam width reducer element for allowing the minimum spot size to be reduced. Although exemplary embodiments illustrating these features have been described herein, alternative embodiments may be provided in accordance with the general principles of the invention. Moreover, other features and advantages of the invention in addition to those specifically cited herein may be apparent to those skilled in the art. Accordingly, the scope of the invention should not be limited to the exemplary embodiments described herein.

We claim:

1. A luminaire for use during a medical procedure, said luminaire comprising:

single fiber optic means for illuminating a surgical field, the single fiber optic means consisting essentially of a single optic fiber for providing a beam of light exiting said single optic fiber having an initial beam energy;

means positioned between the single optic fiber and said surgical field for adjusting a width of the beam exiting said single optic fiber without substantially decreasing the beam energy; and means positioned between the single optic fiber and said surgical field for directing the beam of adjusted width from said single optic fiber onto said surgical field.

2. The luminaire of claim 1, wherein the means for adjusting the width of the beam comprises:

a first optical system positioned along a path of the beam of light between the means for providing light and the means for directing the beam;

a second optical system positioned between the first optical system and the means for directing the beam; and means for displacing the first optical system with respect to the second optical system; wherein the first and second optical systems are configured for varying a width of the beam with relative displacement of the first and second optical systems.

3. The luminaire of claim 2, wherein the first and second optical systems are doublet lenses.

4. The luminaire of claim 1, wherein said means for directing the beam directs the beam at an angle of 110–130 degrees from an axis along which the single fiber optic means for providing the beam of light provides the beam.

5. The luminaire of claim 4, wherein said means for directing the beam is a mirror with a normal oriented at an angle of 50–70 degrees from the axis.

6. The luminaire of claim 1 further including a filter mounted within a path of the beam for altering the spectral characteristics of the beam.

7. A luminaire for use during a medical procedure, said luminaire comprising fiber optic means for providing a beam of light having an initial beam width and an initial beam energy, means for adjusting the width of the beam without substantially decreasing the beam energy, and means for directing the beam of adjusted width onto a surgical field, for use with a surgical loupe, wherein said luminaire is mounted adjacent said surgical loupe, and wherein the luminaire further includes:

a first linear polarizer within a path of the beam of light for polarizing the beam of light;

a second linear polarizer within the loupe; and wherein said first and second linear polarizers are rotatable with respect to one another.

8. A luminaire for use during a medical procedure, said luminaire comprising single fiber optic means for providing a beam of light having an initial beam width and an initial beam energy, means for adjusting a width of the beam of light without substantially decreasing the beam energy, and means for directing the beam of light having adjusted width onto a surgical field, wherein the single fiber optic means for providing the beam of light is a primary optic fiber and wherein the luminaire further includes:

a fiber optic beam width reducer, mounted directly to a transmission end of the primary optic fiber, for reducing the width of the beam of light transmitted from the primary optic fiber, said fiber optic beam width reducer having an optic fiber having a width narrower than a width of the primary optic fiber.

9. A surgical luminaire, comprising a single fiber optic means consisting essentially of a single optic fiber for delivering a beam of light, and having means for directing and adjusting the beam of light exiting said single optic fiber on a field requiring illumination, said means for adjusting and directing being positioned between the single optic fiber and the field requiring illumination, said luminaire further comprising:

two lens systems sharing an optical axis within a path of the beam of light exiting said single optic fiber;

linear displacement means for adjusting a relative distance between the two lens systems such that linear motion of the two lens systems changes an illuminated spot size of light exiting said single optic fiber without rotating said single fiber optic means, said two lens systems configured to provide a maximum spot size when positioned adjacent to one another and a minimum spot size when displaced by a sufficient amount to image a distal end of the single fiber optic means; and a mirror angled at 50° to 70° relative to the optical axis for reflecting light exiting said single optic fiber and transmitted through the two lens systems onto the field requiring illumination.

10. The luminaire of claim 9, wherein a first lens system of the two lens systems is mounted in a fixed relationship with the single optic fiber and wherein the displacement means displaces a second lens system of the two lens systems relative to the single optic fiber and to the first lens system.

11. The invention of claim 10, wherein both of the lens systems are doublet lenses.

12. The luminaire of claim 9, wherein the means for directing a beam of light onto a surgical field, includes:

a filter means within a path of the beam of light for altering the spectral characteristics of the beam of light.

13. The luminaire of claim 9, further comprising:

a fiber optic beam width reducer mounted directly to a transmission end of said single optic fiber, said single optic fiber being a primary optic fiber, said fiber optic beam width reducer for reducing the width of the beam of light transmitted from the primary optic fiber, said fiber optic beam width reducer having an optic fiber having a width narrower than a width of the primary optic fiber.

14. A surgical luminaire, having fiber optic means for delivering a beam of light, and means for directing and adjusting the beam of light to form an illuminated spot on a field requiring illumination, said spot having an illuminated spot size, said luminaire comprising:

two lens systems sharing an optical axis within a path of the beam of light;

linear displacement means for adjusting a relative distance between the two lens systems such that linear motion of the two lens systems changes the illuminated spot size without rotating said fiber optic means, said two lens systems configured to provide a maximum spot size when positioned adjacent to one another and a minimum spot size when displaced by a sufficient amount to image a distal end of the fiber optic means; and a mirror angled at 50° to 70° relative to the optical axis for reflecting light transmitted through the two lens systems onto the field requiring illumination, mounted adjacent a surgeon's viewing device, wherein the luminaire further includes:

a first linear polarizer within a path of the beam of light for polarizing the beam of light; and a second linear polarizer within the viewing device; and wherein said first and second linear polarizers are rotatable with respect to one another.

15. A luminaire for use with a viewing device, said luminaire comprising:

a primary optic fiber means providing a beam of light having an initial beam width and an initial beam energy;

a mirror for reflecting the beam of light onto a surgical field to provide a spot of light on the surgical field;

a first optical system positioned along a path of the beam of light between the first optical system and the mirror;

a second optical system positioned between the first optical system and the mirror; and a mechanical positioning system interconnected to the first optical system and the second optical system for displacing the primary optic fiber means and the first optical system with respect to the second optical system, wherein the first and second optical systems are configured for varying the beam width by relative displacement of the first and second optical systems to vary the size of the spot of light on the surgical field, and wherein the luminaire further includes:

a first linear polarizer within a path of the beam of light for polarizing the beam of light; and a second linear polarizer within the viewing device the viewing device positioned between the surgical field and a viewer's eye; and wherein said first and second linear polarizers are rotatable with respect to one another.

16. A luminaire for use during a medical procedure, said luminaire comprising:

a primary optic fiber means consisting essentially of a single optic fiber providing a beam of light having an initial beam width and an initial beam energy;

a mirror for reflecting the beam of light onto a surgical field to provide a spot of light on the surgical field;

a first optical system positioned along a path of the beam of light between the first optical system and the mirror;

a second optical system positioned between the first optical system and the mirror; and a mechanical positioning system interconnected to the first optical system and the second optical system for displacing the primary optic fiber means and the first optical system with respect to the second optical system, wherein the first and second optical systems are configured for varying the beam width by relative displacement of the first and second optical systems to vary the size of the spot of light the surgical field, said luminaire further including:

a fiber optic beam width reducer, mounted directed to a transmission end of the primary optic fiber means, for reducing width of the beam of light transmitted from the primary optic fiber means, said fiber optic beam width reducer having an optic fiber having a width narrower than a width of the primary optic fiber means.

17. A headband for mounting a luminaire to a surgeon's head, the headband comprising:

a head strap consisting essentially of a perspiration-absorbent cloth strip sized for fitting around a surgeon's head;

engageable hook and clasp members attached to opposing ends of said head strap, wherein said head strap fits snugly around the surgeon's head with said hook and clasp members engaged;

a luminaire-mounting member connected to the head strap and configured for mounting a luminaire to said head strap; and a clasp for securing a fiber optic light guide extending from the luminaire above a rear portion of the head of the surgeon;

said luminaire-mounting member comprising a pocket in a middle portion of said head strap, said pocket configured for receiving a contoured rear plate of said luminaire for mounting said luminaire along a front portion of the surgeon's head, wherein said clasp is attached to the strap adjacent one of the opposing ends of said head strap.

18. The headband of claim 17 in combination with a luminaire for directing a beam of light onto a surgical field, said luminaire being mounted to said headband with said luminaire mounting member, said luminaire further including a fiber optic light guide secured to said clasp.

* * * * *